US00PP28392P3

(12) United States Plant Patent
Rijk

(10) Patent No.: US PP28,392 P3
(45) Date of Patent: Sep. 12, 2017

(54) ***NEMESIA* PLANT NAMED 'FIANGPEACIMP'**

(50) Latin Name: *Nemesia hybrida*
Varietal Denomination: Fiangepeacimp

(71) Applicant: Nadine Rijk, De Lier (NL)

(72) Inventor: Nadine Rijk, De Lier (NL)

(73) Assignee: Dümmen Group B.V., De Lier (NL)

( * ) Notice: Subject to any disclaimer, the term of this patent is extended or adjusted under 35 U.S.C. 154(b) by 139 days.

(21) Appl. No.: 14/545,633

(22) Filed: May 29, 2015

(65) Prior Publication Data

US 2016/0353647 P1 Dec. 1, 2016

(51) Int. Cl.
*A01H 5/02* (2006.01)

(52) U.S. Cl.
USPC ..... Plt./458

(58) Field of Classification Search
USPC ..... Plt./263.1, 458
See application file for complete search history.

(56) References Cited

PUBLICATIONS

PLUTO: Plant Variety Database, Nov. 11, 2016, citation for 'Fiangpeacimp'. 1 page.*

* cited by examiner

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Nemesia* plant named 'Fiangpeacimp', characterized by its upright, outwardly spreading and uniformly mounded growth habit; freely branching and flowering plant habit; orange and light red purple-colored flowers; and good garden performance.

1 Drawing Sheet

Botanical designation: *Nemesia hybrida.*
Cultivar denomination: 'FIANGPEACIMP'.

BACKGROUND OF THE INVENTION

The present invention relates to a new and distinct cultivar of *Nemesia* plant, botanically known as *Nemesia hybrida* and hereinafter referred to by the name 'Fiangpeacimp'.

The new *Nemesia* plant is a product of a planned breeding program conducted by the Inventor in Tochigi, Japan. The objective of the breeding program is to create new freely-branching and flowering *Nemesia* plants with attractive flower colors.

The new *Nemesia* plant originated from a cross-pollination made by the Inventor in 2011 of two unidentified proprietary selections of *Nemesia hybrida*. The new *Nemesia* plant was discovered and selected by the Inventor as a single flowering plant from within the progeny of the stated cross-pollination in a controlled greenhouse environment in Tochigi, Japan in 2011.

Asexual reproduction of the new *Nemesia* plant by terminal cuttings in a controlled environment in Tochigi, Japan since 2011 has shown that the unique features of this new *Nemesia* plant are stable and reproduced true to type in successive generations.

SUMMARY OF THE INVENTION

Plants of the new *Nemesia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Fiangpeacimp'. These characteristics in combination distinguish 'Fiangpeacimp' as a new and distinct *Nemesia* plant:

1. Upright, outwardly spreading and uniformly mounded growth habit.
2. Freely branching and flowering plant habit.
3. Orange and light red purple bi-colored flowers.
4. Good garden performance.

Plants of the new *Nemesia* can be compared to plants of the parent selections. Plants of the new *Nemesia* differ primarily from plants of the parent selections in the following characteristics:

1. Plants of the new *Nemesia* are more compact and more uniform than plants of the parent selections.
2. Plants of the new *Nemesia* are more freely branching than plants of the parent selections.

Plants of the new *Nemesia* can also be compared to plants of the *Nemesia caerulea*×*Nemesia strumosa* 'Kirine-15', disclosed in U.S. Plant Pat. No. 18,270. In side-by-side comparisons, plants of the new *Nemesia* differed primarily from plants of 'Kirine-15' in the following characteristics:

1. Plants of the new *Nemesia* were shorter than plants of 'Kirine-15'.
2. Plants of the new *Nemesia* were more freely branching than plants of 'Kirine-15'.
3. Leaves of plants of the new *Nemesia* were broader than leaves of plants of 'Kirine-15'.
4. Plants of the new *Nemesia* and 'Kirine-15' differed in flower color as plants of 'Kirine-15' had orange-colored flowers.

BRIEF DESCRIPTION OF THE PHOTOGRAPH

The accompanying colored photograph illustrates the overall appearance of the new *Nemesia* plant showing the colors as true as it is reasonably possible to obtain in colored reproductions of this type. Colors in the photograph may differ slightly from the color values cited in the detailed botanical description which accurately describe the colors of the new *Nemesia* plant.

The photograph is a side perspective view of a typical flowering plant of 'Fiangpeacimp' grown in a container.

DETAILED BOTANICAL DESCRIPTION

Plants used for the aforementioned photograph and following description were grown under environmental conditions and cultural practices which closely approximate commercial production conditions during the summer in 12-cm containers in a glass-covered greenhouse in Rheinberg, Germany. During the production of the plants, day temperatures ranged from 17° C. to 30° C. and night temperatures ranged from 10° C. to 20° C. Plants were pinched about two weeks after planting and were eight weeks old when the photograph and description were taken. In the following description, color references are made to The Royal Horticultural Society Colour Chart, 2007 Edition, except where general terms of ordinary dictionary significance are used.

Botanical classification: *Nemesia hybrida* 'Fiangpeacimp'.

Parentage:

*Female, or seed, parent*.—Unidentified proprietary selection of *Nemesia hybrida*, not patented.

*Male, or pollen, parent*.—Unidentified proprietary selection of *Nemesia hybrida*, not patented.

Propagation:

*Type*.—By vegetative terminal cuttings.

*Time to initiate roots, summer and winter*.—About seven days at temperatures about 22° C. to 30° C.

*Time to produce a rooted young plant, summer*.—About twelve days at temperatures about 22° C. to 30° C.

*Time to produce a rooted young plant, winter*.—About two weeks at temperatures about 20° C. to 25° C.

*Root description*.—Medium in thickness, fibrous; greyed white in color.

*Rooting habit*.—Moderately freely branching; medium density.

Plant description:

*Plant and growth habit*.—Upright, outwardly spreading and uniformly mounded growth habit; freely branching habit with about five primary lateral branches developing per plant; pinching enhances lateral branch development; moderately vigorous growth habit.

*Plant height*.—About 12 cm.

*Plant diameter*.—About 23 cm.

Lateral branch description:

*Length*.—About 10 cm.

*Diameter*.—About 2 mm.

*Internode length*.—About 1 cm to 1.5 cm.

*Strength*.—Moderately strong.

*Aspect*.—Upright to outwardly spreading.

*Texture*.—Sparsely pubescent.

*Color*.—Close to 143C.

Leaf description:

*Arrangement*.—Opposite, simple.

*Length*.—About 3.2 cm.

*Width*.—About 1 cm.

*Shape*.—Lanceolate.

*Apex*.—Acute.

*Base*.—Attenuate.

*Margin*.—Serrate.

*Texture, upper and lower surfaces*.—Smooth, glabrous.

*Venation pattern*.—Pinnate; arcuate.

*Color*.—Developing leaves, upper and lower surfaces: Close to 143B. Fully expanded leaves, upper surface: Close to 141B; venation, close to 141B. Fully expanded leaves, lower surface: Close to 141C; venation, close to 141C.

*Petioles*.—Length: About 3 mm. Diameter: About 5 mm. Texture, upper and lower surfaces: Smooth, glabrous. Color, upper surface: Close to 144A. Color, lower surface: Close to 146C.

Flower description:

*Flower arrangement and flowering habit*.—Zygomorphic bilabiate flowers arranged on loose terminal racemes; flowering acropetally towards the apex; flowers face mostly outwardly; freely flowering habit with about 16 flowers per raceme and about 900 flowers developing per plant during the flowering season.

*Flower longevity*.—Individual flowers last about four to five days on the plant; flowers not persistent.

*Fragrance*.—None detected.

*Natural flowering season*.—In Northern Europe, plants flower continuously from May to September; plants begin flowering about seven weeks after planting.

*Inflorescence height*.—About 4 cm.

*Inflorescence diameter*.—About 4.2 cm.

*Flower length*.—About 2.8 cm.

*Flower diameter*.—About 2.2 cm.

*Flower depth*.—About 1.5 cm.

*Flower buds*.—Length: About 8.6 mm. Diameter: About 6.8 mm. Shape: Ovoid. Texture: Pubescent. Color: Close to 31C and 47C.

*Petals*.—Arrangement: Five petals; four upper petals are fused at base to form an upright lobed and arched banner lip; lower petal modified into a larger lip with convex oval protuberance with serves as a pollinator nectar guide and landing platform. Shape: Oval to rounded. Apex: Rounded. Margin: Entire. Length: About 1 cm to 1.5 cm. Width: About 5 mm to 15 mm. Texture, upper and lower surfaces: Smooth, glabrous. Color: When opening and fully opened, upper surface: Close to N25C and 63A; colors do not fade with development. When opening and fully opened, lower surface: Close to 23B and 63B; colors do not fade with development.

*Sepals*.—Arrangement: Calyx star-shaped with five sepals fused at the base. Length: About 4 mm. Width: About 1 mm. Shape: Elliptical. Apex: Acute. Margin: Entire. Texture, upper and lower surfaces: Pubescent. Color, upper and lower surfaces: Close to 143A.

*Peduncles*.—Length: About 5 cm to 6 cm. Diameter: About 2 mm. Angle: Erect to about 45° from vertical. Strength: Strong. Texture: Sparsely pubescent. Color: Close to 146B.

*Pedicels*.—Length: About 1 cm to 1.5 cm. Diameter: About 1 mm. Angle: About 30° to 45° from peduncle axis. Strength: Strong. Texture: Sparsely pubescent. Color: Close to 143A.

*Reproductive organs*.—Stamens: Quantity: Four per flower. Filament length: About 1 mm to 4 mm. Filament color: Close to N155A. Anther shape:

Oval. Anther length: Less than 1 mm. Anther color: Close to 142A. Pollen amount: Scarce. Pollen color: Close to 17B. Pistils: Quantity: One per flower. Pistil length: About 2 mm. Style length: About 1 mm. Style color: Close to 142A. Stigma shape: Rounded. Stigma color: Close to 142A. Ovary color: Close to 142A.

*Seeds and fruits*.—Seed and fruit development have not been observed on plants of the new *Nemesia* to date.

Pathogen & pest resistance: Plants of the new *Nemesia* have not been observed to be resistant to pests and pathogens common to *Nemesia* plants.

Garden performance: Plants of the new *Nemesia* have been observed have good garden performance and to tolerate wind, rain and temperatures ranging from 4° C. to 35° C.

It is claimed:

1. A new and distinct *Nemesia* plant named 'Fiangpeacimp' as illustrated and described.

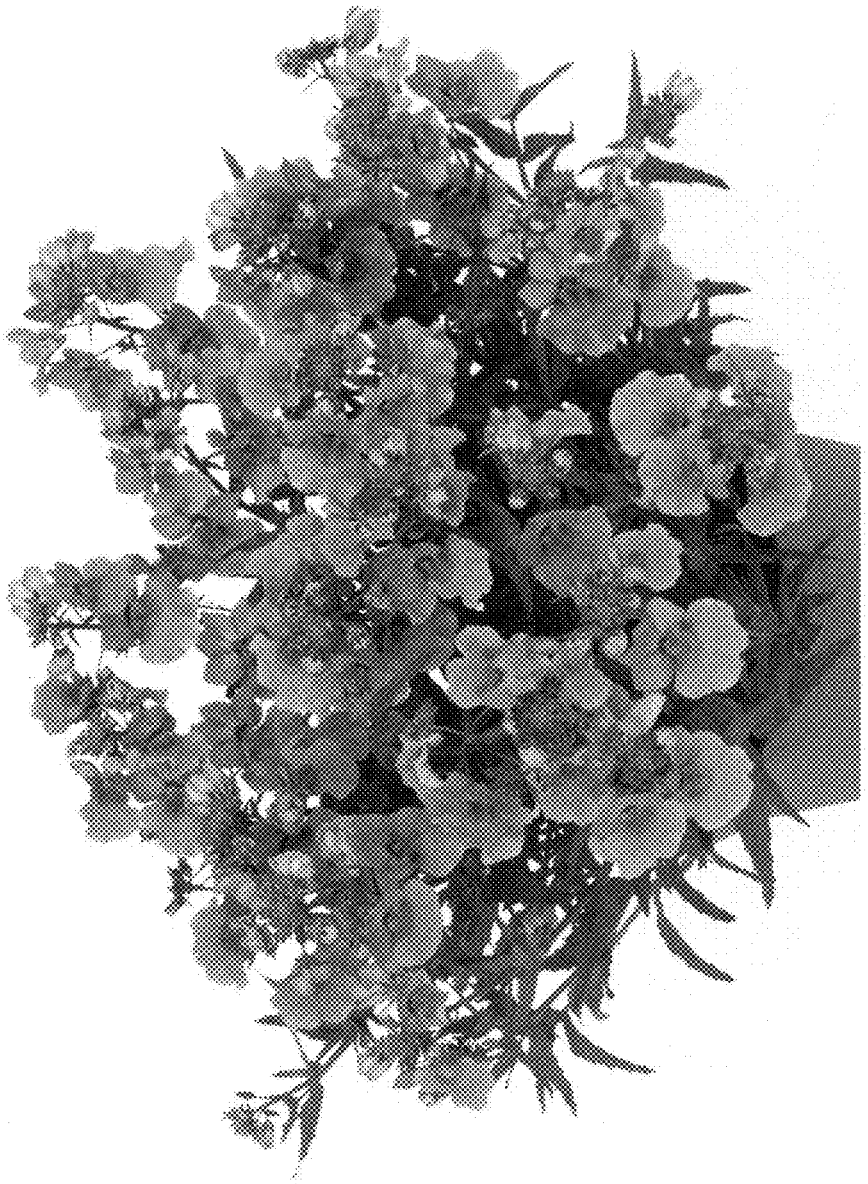

* * * * *